United States Patent
Haarala et al.

(10) Patent No.: US 7,033,335 B2
(45) Date of Patent: Apr. 25, 2006

(54) GUIDEWIRE COMPATIBLE PORT AND METHOD FOR INSERTING SAME

(75) Inventors: Brett Haarala, Watertown, MA (US); William Shaw, Cambridge, MA (US); Chris Davey, Boston, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 10/462,758

(22) Filed: Jun. 17, 2003

(65) Prior Publication Data

US 2003/0229323 A1    Dec. 11, 2003

Related U.S. Application Data

(60) Continuation of application No. 09/231,075, filed on Jan. 14, 1999, now Pat. No. 6,613,013, which is a division of application No. 08/941,919, filed on Oct. 1, 1997, now Pat. No. 6,190,352.

(51) Int. Cl.
*A61M 11/00* (2006.01)

(52) U.S. Cl. .............................. 604/93.01; 604/288.02; 604/502

(58) Field of Classification Search ............. 604/93.01, 604/116, 164.12, 167.01–167.06, 174, 175, 604/201, 244, 288.02, 500, 502, 523, 524
See application file for complete search history.

(56) References Cited

U.S. PATENT DOCUMENTS

| | | | |
|---|---|---|---|
| 3,757,771 A | * | 9/1973 | Ruegg et al. ............... 600/360 |
| 4,543,088 A | | 9/1985 | Bootman et al. |
| 4,692,146 A | | 9/1987 | Hilger |
| 4,710,174 A | | 12/1987 | Moden et al. |
| 4,886,501 A | | 12/1989 | Johnston et al. |
| 4,892,518 A | | 1/1990 | Cupp et al. |
| 5,084,015 A | * | 1/1992 | Moriuchi ............... 604/288.02 |
| 5,250,033 A | | 10/1993 | Evans et al. |
| 5,263,930 A | | 11/1993 | Ensminger |
| 5,267,958 A | * | 12/1993 | Buchbinder et al. ... 604/103.14 |
| 5,281,199 A | | 1/1994 | Ensminger et al. |
| 5,318,545 A | | 6/1994 | Tucker |
| 5,360,407 A | | 11/1994 | Leonard |
| 5,385,541 A | * | 1/1995 | Kirsch et al. ................ 604/8 |
| 5,503,630 A | | 4/1996 | Ensminger et al. |
| 5,554,118 A | | 9/1996 | Jang |
| 5,613,945 A | | 3/1997 | Cai et al. |
| 5,743,873 A | | 4/1998 | Cai et al. |
| 5,792,104 A | | 8/1998 | Speckman et al. |
| 6,001,078 A | | 12/1999 | Reekers |

OTHER PUBLICATIONS

Ideas for Machine, Inc., "Ideas' Port Low Profile, Lightweight", 4 pages.

* cited by examiner

*Primary Examiner*—Kevin C. Sirmons
(74) *Attorney, Agent, or Firm*—Finnegan, Henderson, Farabow, Garrett & Dunner, LLP

(57) ABSTRACT

An access port assembly having an attachable catheter allows for inserting a guidewire into the catheter to aid in the placement of the integral catheter while still attached to the access port assembly. A method is described for placing an access port fixedly attached to a catheter into a patient using a guidewire inserted into the catheter.

10 Claims, 13 Drawing Sheets

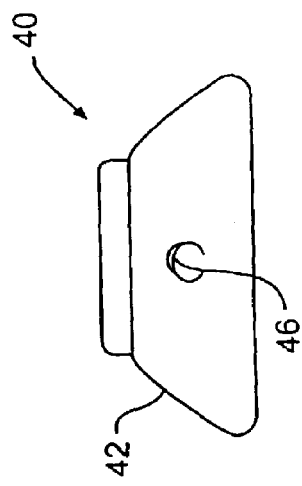
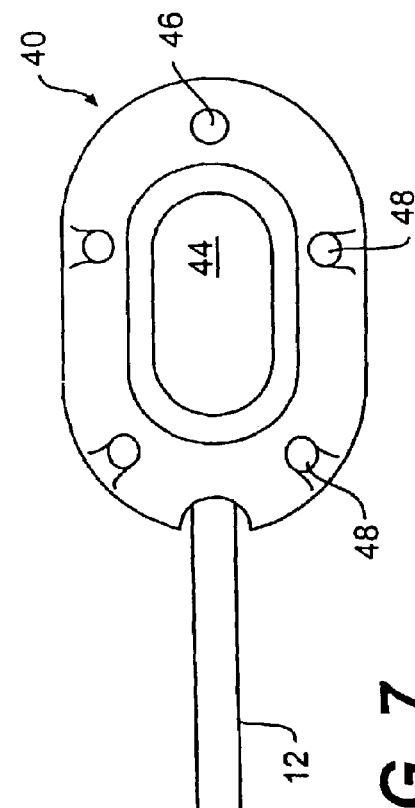
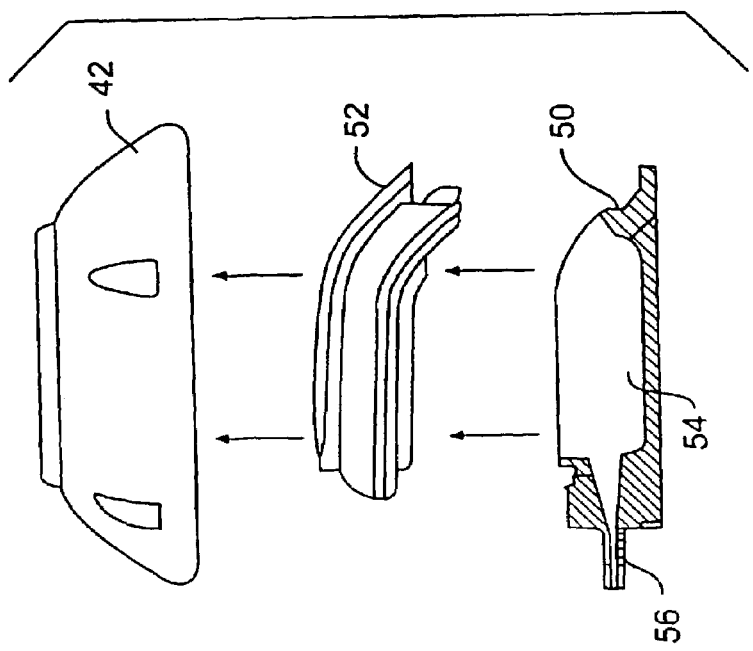
FIG. 8
FIG. 7
FIG. 9

GUIDEWIRE COMPATIBLE PORT AND METHOD FOR INSERTING SAME

This is a continuation of application Ser. No. 09/231,075, filed Jan. 14, 1999, now U.S. Pat. No. 6,613,013, which is a division of application Ser. No. 08/941,919, filed Oct. 1, 1997, now U.S. Pat. No. 6,190,352, all of which are incorporated herein by reference.

BACKGROUND OF THE INVENTION

The present invention relates to an implantable access port assembly which includes an attachable catheter. The present invention further relates to an access port usable with an attachable catheter that may be inserted into a patient as a unit using a guidewire, the unit having an entry site for a guidewire.

An access port connected to a catheter is used to provide an easily accessible site by which fluids can be easily introduced into or extracted from a remote site in a patient. To place an access port and catheter, a catheter is introduced into a vein, artery, existing lumen, created lumen or into other locations in the patient. A guidewire may first be used to facilitate the positioning of the catheter in the patient. Whether a guidewire is used to place the catheter depends on the characteristics of the catheter, the patient's anatomy at the access point, any constrictions in the catheter's pathway and the like. Where a guidewire is used to help position the catheter, it is first inserted into the patient and advanced to the intended location. Once the guidewire is in place, the catheter is threaded on and positioned over the guidewire in the desired location and the guidewire removed, an access port is then attached to the catheter and inserted into a "surgical pocket" in the patient at the access site. The attachment of the access port to the catheter can, however, be difficult due to the lubricious nature of the catheter and access port during insertion. Additionally, the physician does not have much maneuverability with the catheter since the distal end of the catheter has been placed at a specific location and the proximal end of the catheter has been cut to a length that optimizes placement of the catheter and access port into the surgical pocket. Therefore, the physician must be careful in manipulating the catheter when attaching the access port.

Additionally, there is a concern that the catheters may become detached from the access port after implantation, causing the fluids not to reach their intended location. Integral ports and catheters have not been used where s guidewire is required to place the catheter since the proximal end of the catheter/access port is closed, thereby preventing withdrawal of the guidewire once the catheter is in place.

Access ports used are usually constructed with a rigid-body such as shown in U.S. Pat. No. 5,613,945. The access ports are made of materials such as titanium, acetal, polysulfone, etc., and have a self-sealing silicone access septum that is accessible percutaneously and through which a needle is inserted to inject or remove fluids from the access port's reservoir. An access port must first be located by palpating the skin at the access site. While a rigid-body access port is easy to find by palpation, a rigid-body has possible drawbacks such as tissue compression and erosion in the overlying layer, discomfort, and the like. The access septum is small relative to the size of access port. However, a smaller access septum results in a higher concentration of needle punctures in a smaller area, which in turn could be painful for the patient and may lead to necrosis of the tissue overlying the access port as well. The smaller access septum also increases the likelihood that the septum "target" will be missed more frequently when attempting to access the septum.

One known soft-bodied access port is made of silicone formed around a wire-mesh support to help it maintain its shape. One problem with this structure is that the wire mesh could interfere with the insertion of a guidewire.

SUMMARY OF THE INVENTION

Accordingly, the present invention is directed to an access port with an attachable catheter that substantially obviates one or more of the problems due to limitations and disadvantages of the related art.

To achieve these and other advantages in accordance with the purpose of the invention, as embodied and broadly described, the invention includes an access port device having a central body portion with a self-sealing access septum and a reservoir, an outlet for fixedly attaching a catheter to the central body, and a self-sealing site, which can be a second septum disposed in the body for inserting a guidewire or a stylet into the reservoir and into the catheter.

In one preferred embodiment the invention also includes an access port assembly having a self-sealing access septum, a catheter integrally attached to the access port and one or more lumens configured to receive a guidewire or stylet for guiding the catheter in a body.

In another preferred embodiment the invention further includes a soft-bodied access port having an access port body and a needle stop disposed in the bottom of a reservoir.

The accompanying drawings, which are incorporated in and constitute a part of this specification, illustrate several embodiments of the invention and, together with the description, serve to explain the principles of the invention.

Additional features and advantages of the invention will be set forth in the description which follows, and in part will be apparent from the description or may be learned by the practice of the invention. The objectives and or other advantages of the invention will be realized and attained by the access port and/or catheter particularly pointed out in the written descriptions and claims hereof, as well as in the accompanying drawings.

BRIEF DESCRIPTION OF THE DRAWINGS

FIG. 7 is a top view of an access port in accordance with a second embodiment of the present invention.

FIG. 8 is a rear view of the access port of FIG. 7.

FIG. 9 is an exploded view of the access port of FIG. 7.

DESCRIPTION OF THE PREFERRED EMBODIMENTS

Reference will now be made in detail to the present embodiments of the invention, and examples which are illustrated in the accompanying drawings. Wherever possible, the same reference numbers will be used throughout the drawings to refer to the same or like parts. It should be understood that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

The present invention represents an improvement over conventional access ports and access port/catheter assemblies. One embodiment of the invention includes an access port with an attachable catheter that allows for a guidewire or stylet to be inserted through the catheter to aid in the placement of the catheter prior to inserting the access port into a pocket in a patient. Another embodiment of the invention includes an access port with an attached catheter and a self-sealing second septum in the access port for inserting a guidewire or stylet into and through the access port and into the attached catheter.

Figure 1:
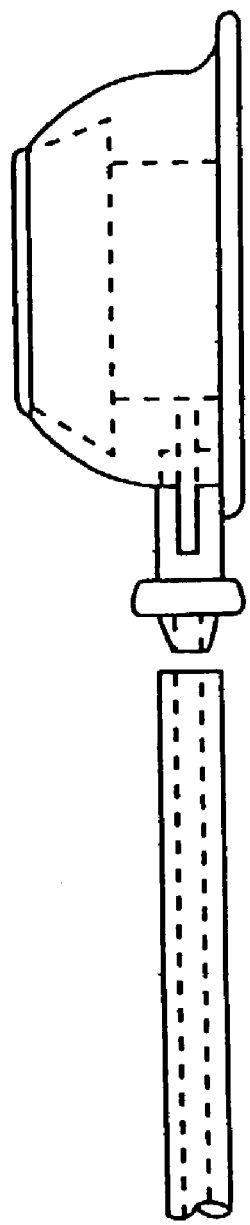
FIG. 1 shows a known access port and attachable catheter.
Figure 1:
Figure 2:
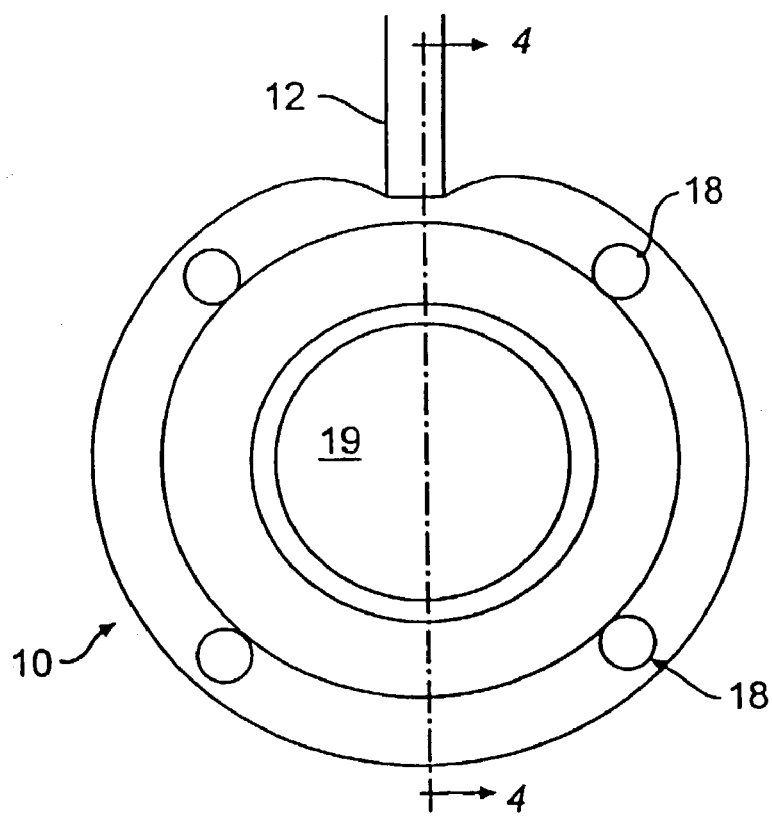
FIG. 2 is a top view of an access port in accordance with a first embodiment of the present invention.
Figure 3:
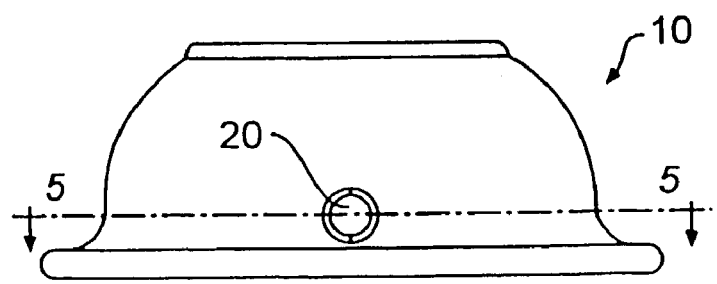
FIG. 3 is a rear view of the access port of FIG. 1.
Figure 4:
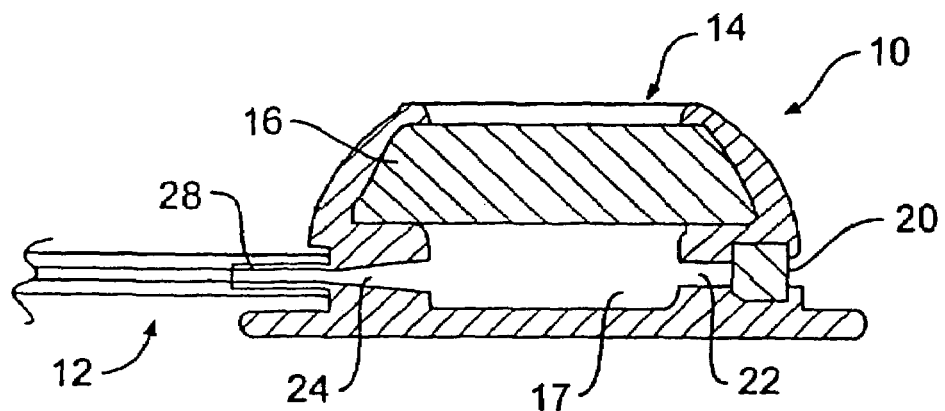
FIG. 4 is a cross sectional view of the access port of FIG. 1.
Figure 5:
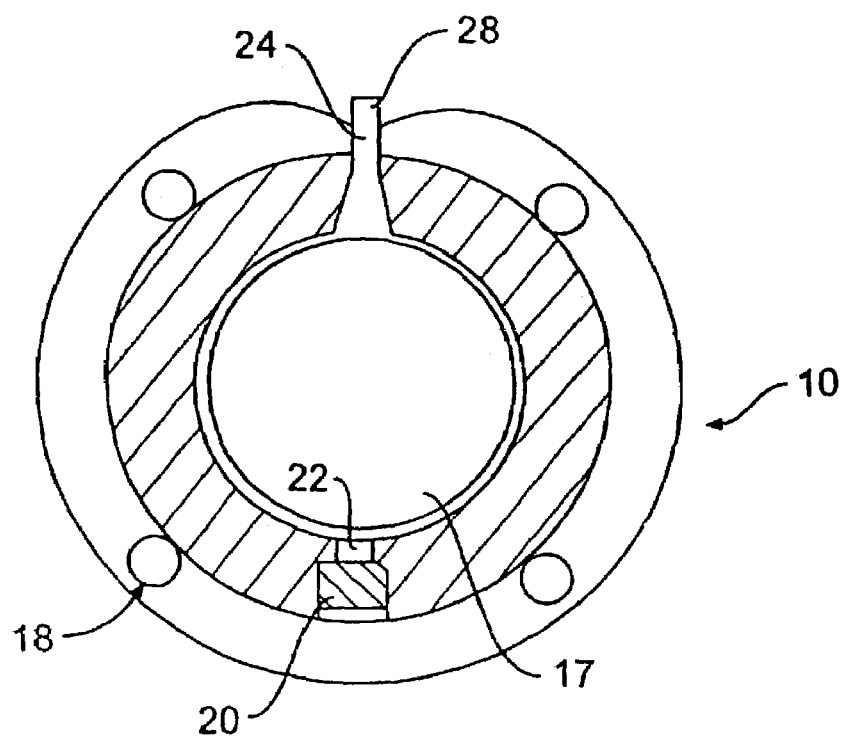
FIG. 5 is a cross sectional view of the access port of FIG. 1.
Figure 6:
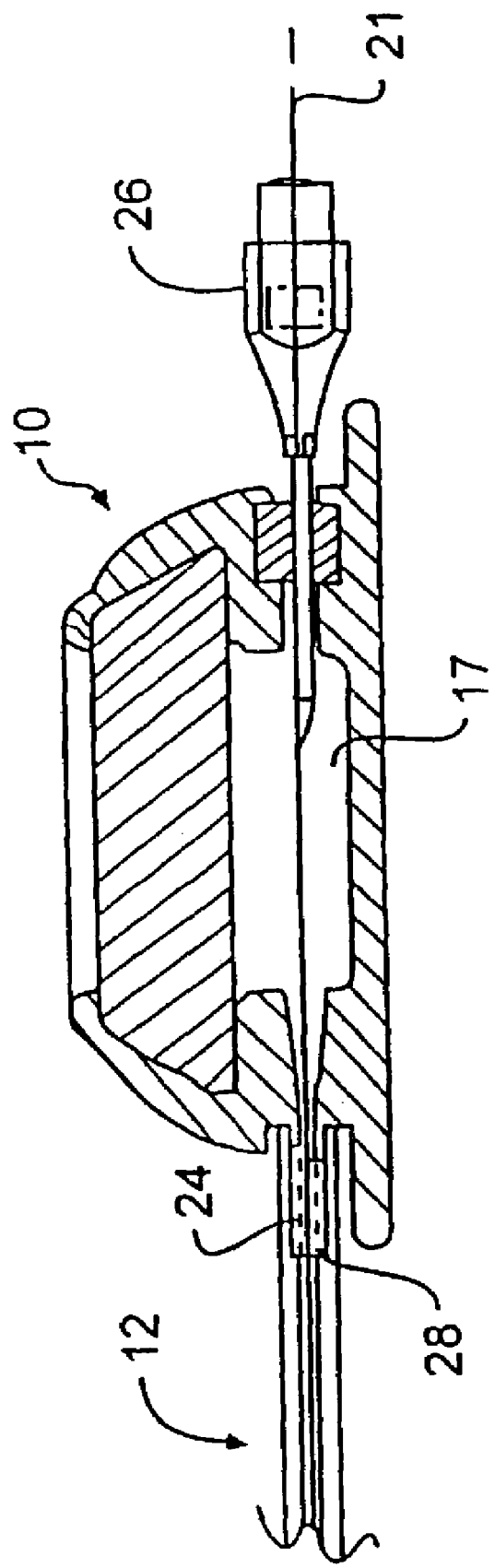
FIG. 6 is another cross sectional view of the access port of FIG. 2 with a needle and guidewire inserted through the access port and into the catheter.

FIGS. 2 to 6 illustrate a first embodiment of an access port 10 with an attachable catheter 12 in accordance with the present invention. Access port 10 is shown from the top in FIG. 2 and has a target area 14 for insertion of a needle (not shown) into a self-sealing access septum 16 (see also FIG. 4). Access port 10 can be made of any material compatible with a long residence time in the patient. Such materials would include, but are not limited to titanium, acetal, and polysulfone. Access port 10 also has a plurality of suture sites 18 for securing the access port 10 into a surgical pocket in the patient (not shown). Preferably, the plurality of suture sites 18 are designed to minimize tissue in-growth and allow for easy removal, such as by reinforcing the sites with solid silicone. Underlying the access septum 16 is a reservoir 17 into which a needle (not shown) may be inserted through the access septum 16 and fluids either injected or removed from the reservoir 17. On the backside of access port 10 is a self-sealing second septum 20 allowing a guidewire 21 (see FIG. 6) to be inserted into the access port 10 through reservoir 17, out outlet 24 of the access port 10, and into catheter 12 as shown in FIG. 6. In order to facilitate the insertion of the guidewire through the self-sealing second septum 20, a non-coring needle 26 of suitable size can be used to make a path through the second septum 20. It is also possible to use other devices that can create an entry through the septum 20, such as a specially-designed cannula or even sufficiently stiff guidewire that can be pushed through the septum 20.

Catheter 12 is fixedly attached to the access port body 10 on an outlet tube 28. The connection between the catheter 12 and outlet tube 28 of access port 10 is intended to be leak-proof and fixed so that the access port is not easily removable from the catheter. The catheter may be attached by bonding the catheter to the outlet tube 28, integrally forming the catheter with the access port body, or using connectors, such as a threaded connector, a pull-actuated connector, and an "interference barb" connector, although other types of connections may be used. Additionally, although not shown in the figures, the catheter 12 may have a thicker wall portion adjacent to the access port 10 or be reinforced to resist kinking of the catheter at outlet tube 28. Reinforcement of the catheter may include, but is not limited to, a reinforcing braid inside the catheter wall, a variable durometer catheter, a catheter using stress relief at the connection, etc. If a thicker walled catheter is used, the catheter 12 may gradually taper to a normal catheter wall thickness downstream from access port 10.

A method for inserting the access port 10 and catheter 12 is achieved in the following manner. Entry into the patient's vessel is made as for any other catheter insertion, using, for example, the Seldinger method. A measuring guidewire (not shown) may be advanced to the desired termination point such as, for example, the superior vena cava of the heart. The distance from the insertion point to the desired location, the superior vena cava, is determined and catheter 12 is then trimmed to the corresponding length. The catheter, depending on the type of connection to the access port, may be trimmed at either end. A pocket is then formed under the skin at the entry point to receive port 10. As shown in FIG. 6, access into the port body, using a non-coring needle 26 for example, is gained through the self-sealing second septum 20 and guidewire 21 is inserted through the non-coring needle 26 into and through the reservoir 17, through outlet 28, and through catheter 12. The distal end of guidewire 21, with the access port/catheter assembly slipped over it, is then inserted into the patient and advanced to the desired location (e.g., superior vena cava). The catheter 12 and port 10 assembly is then advanced over the guidewire 21 until the tip of catheter 12 is positioned at the desired location along the guidewire. The guidewire 21 and non-coring needle 26 are removed from the self-sealing second septum 20. The access port 10 and reservoir 17 are accessed through the access septum 16 with a non-coring needle (not shown) and flushed to ensure proper operation. The access port 10 is then sutured into place using suture sites 18. The incision used to create the pocket is then closed, concealing the access port 10. The guidewire can also be inserted into the patient and then the access port/catheter slid over the catheter.

A second embodiment of the invention is shown in FIGS. 7–9. As shown in those figures, access port 40 has an upper body 42, a target area 44, a plurality of suture sites 48, and a hole 46 for inserting a needle (not shown) and guidewire (not shown) into and through the access port 40 and into catheter 12 as in the first embodiment. As shown in FIG. 9, the access port 40 is made of three pieces: upper body 42, lower body 50, and a self-sealing access septum 52. Self-sealing access septum 52 preferably fits snugly into upper body 42 and creates a reservoir area 54 between the access septum 52 and lower body 50. As with the first embodiment, catheter 12 is attached to the lower body 50 at outlet port 56. Although not shown, a stiff guidewire or a non-coring needle as described for the first embodiment can be inserted into the hole 46 (FIG. 8) in the upper body 42 and through the self-sealing access septum 52 to provide a path for a guidewire (not shown) into and through access port 40 and through output port 56 into the catheter 12. As in the first embodiment, the access port bodies 42 and 50 could be made of a relatively firm or hard biocompatible material such as acetal, titanium, and polysulfone. The insertion of access port 40 into a patient is performed in a manner similar to that described above for access port 10.

Figure 10:
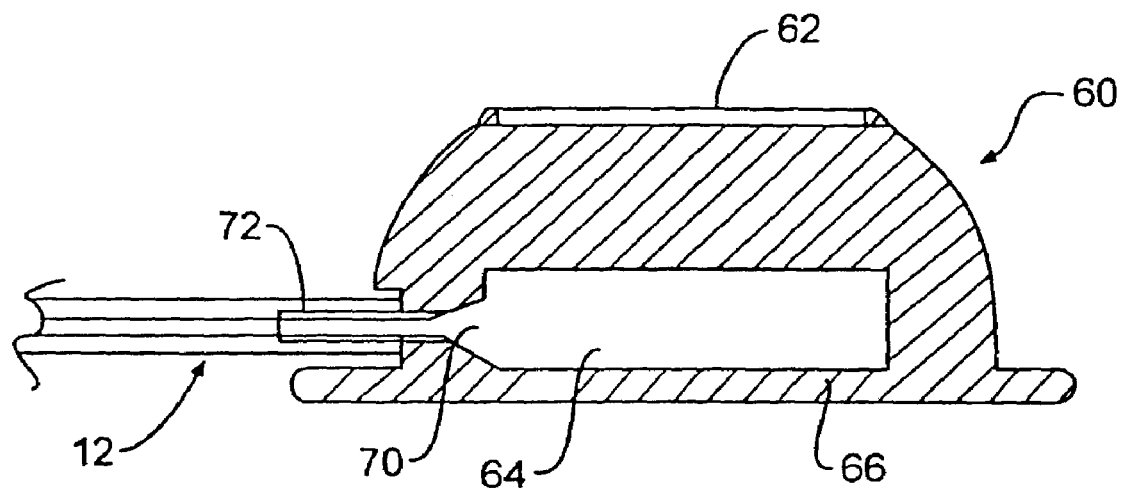
FIG. 10 is a cross sectional view of an access port in accordance with a third embodiment of the present invention.
Figure 11:
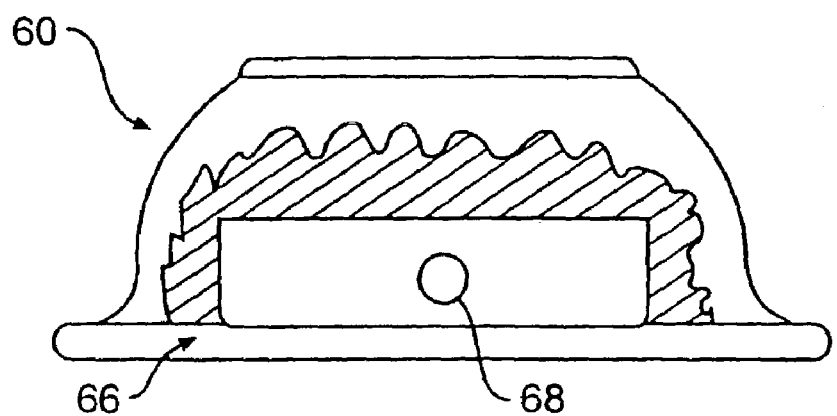
FIG. 11 is a partial cut away in a rear view of the access port of FIG. 10.

A third embodiment of the invention is shown in FIGS. 10 and 11. This third embodiment of the access port 60 is a soft-bodied port, e.g., made of silicone, or other appropriate materials that provide characteristics such as self-sealing and long residence times. Access port 60 is generally shaped as in the first embodiment illustrated in FIGS. 2–7 and also has a target area 62 through which a needle can be inserted to inject or remove fluids from reservoir area 64. Additionally, access port 60 has a rigid insert 66 which extends under and around reservoir area 64 and guidewire access hole 68 in an open configuration which can have sides to form a shallow dish or tray. The rigid insert 66, made from titanium or other rigid material, provides an indication to a person inserting a needle into the access port 60 that the needle has reached the reservoir area 64 and the fluids can be injected or removed as needed (needle stop). The advantage of a soft-bodied access port such as access port 60 is that when a needle hits the hard needle stop 66, the person knows that the needle tip is in the reservoir. With a hard-bodied access port, there is a possibility that the needle has missed the access system and the hard surface that is encountered is the outside surface of the hard-body access port. Thus, the soft-bodied access port eliminates the uncertainty in locating the reservoir 64.

As shown in a partial cutaway of FIG. 11, the rigid insert 66 may have a hole 68 providing access to a needle and/or guidewire to aid in the insertion of the guidewire into the catheter 12, as in the first two described embodiments of the invention. It should be noted that the outlet area 70 is shaped to guide the guidewire into catheter 12. Although not shown, the rigid insert 66 may stop below the outlet 24.

A raised circular area, concentric circles, or some other way of marking (not shown) the location of hole 68 can be made on the back side of the access port 60. Alternatively, the guidewire and/or needle can be pre-inserted, thereby reducing the possibility of missing the hole 68 or the outlet 24 by the physician.

Figure 23:
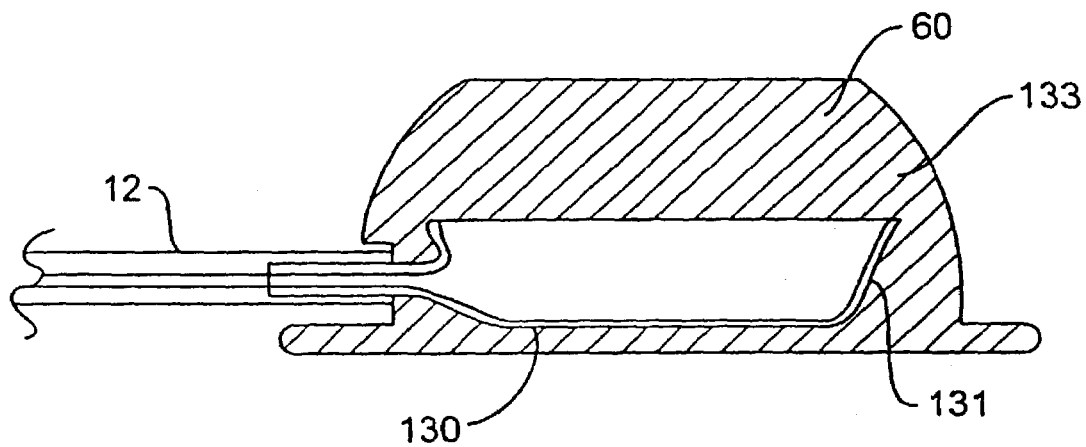
FIG. 23 is a side view of an access port and catheter in accordance with an eighth embodiment of the present invention.
Figure 24:
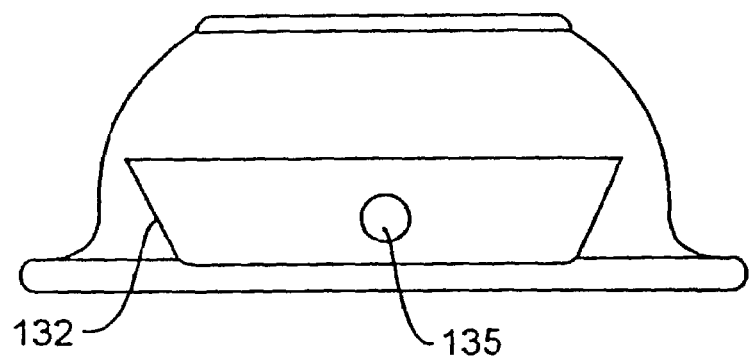
FIG. 24 is a rear view of the access port of FIG. 23.

FIGS. 23 and 24 illustrate the embodiment of the invention where rigid insert 130 in soft-bodied access port 60 has slopping sides 131 and 132 to increase the angle of access through the septum 133. As with the previously discussed third embodiment, the rigid insert 130 can have sides to form a dish or tray and the back side 131 of the insert can be provided with a hole 135 and target indicia (not shown) to facilitate proper alignment of a guidewire or needle.

It should be also noted that access port 60 need not be used in conjunction with the guidewire access hole 68 and attached catheter 12, but can also be used with a detachable catheter and catheter connector (not shown) on outlet 72, thereby eliminating the need for access hole 68. One advantage of using soft bodied access port 60 having a hardened insert over other access ports is that when a needle contacts the hard insert, there is little doubt that the needle is in the reservoir area 64 as discussed above. Additionally, a soft body port produces less compression on the subdermis and may reduce erosion of this layer.

Figure 12:
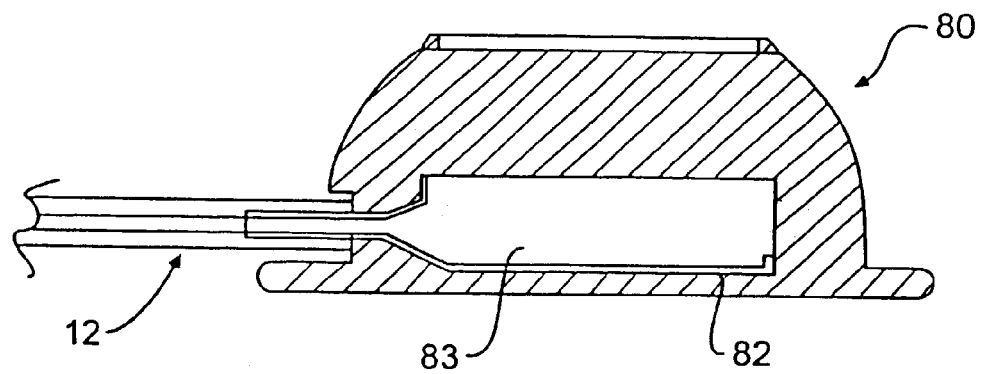
FIG. 12 is a cross sectional view of an access port in accordance with a fourth embodiment of the present invention.
Figure 13:
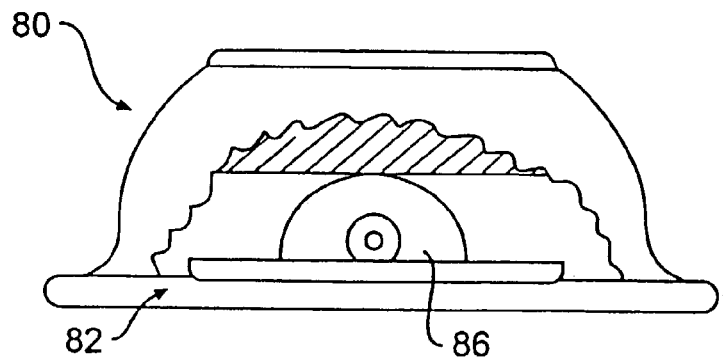
FIG. 13 is a partial cut away in a rear view of the access port of FIG. 12.
Figure 14:
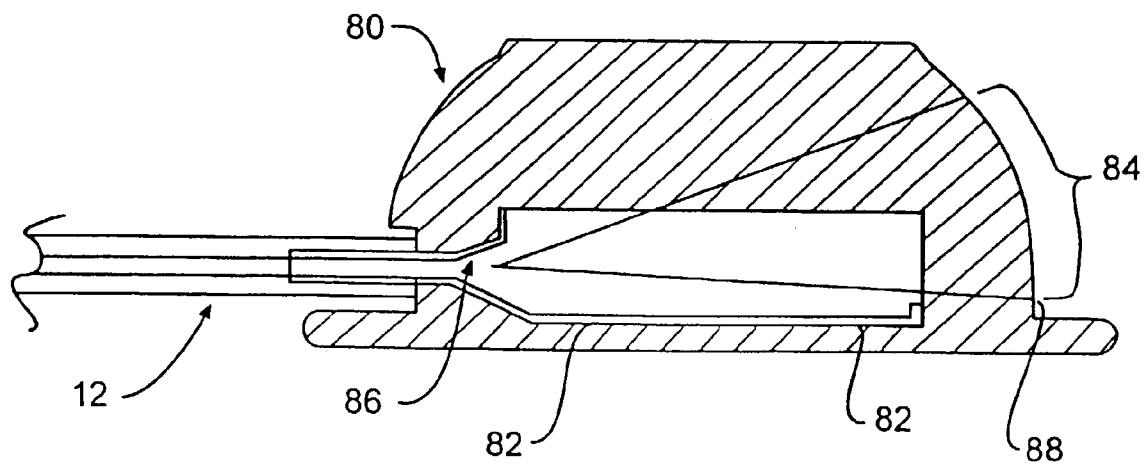
FIG. 14 is cross sectional view of the access port of FIG. 12.

A fourth embodiment of the present invention is shown in FIGS. 12 and 13. Access port 80 is substantially similar to the embodiment shown in FIGS. 10 and 11. However, the rigid insert 82 does not extend upwardly as far at the back side of the reservoir area 83 or have the self-sealing guidewire access hole 68 as shown in FIG. 11. Rather, a needle with a guidewire or a stiff guidewire could be inserted anywhere in the area 84 as shown in FIG. 14. An inserted needle and guidewire is generally directed toward the catheter 12 and guided into the lumen of catheter 12 by the narrowing area 86 shown in FIG. 13. Alternatively, concentric circles or other markings could be used on the back side of access port 80, opposite area 86, to indicate a proper area for inserting the needle and guidewire. Such a marking may also include a horizontal line along the back side of access port 80 to indicate the height of the rigid body 82 at the backside of reservoir 83.

An alternative embodiment of the invention for allowing a guidewire to be used with an access port and catheter is shown in FIGS. 15–22. As previously described, prior art practice has involved first inserting the guidewire into the patient, then slipping the catheter alone over the guidewire and positioning it and then removing the guidewire before attaching the access port to the catheter. In accordance with the described embodiment of the present invention, the guidewire is inserted directly into a lumen of the catheters shown in FIGS. 15–22 with the access port already in place and subsequently withdrawn in the same manner once the catheter is in position. In this embodiment, whereby the guidewire is passed directly into a lumen of the catheter, any access port can be attached to the catheter since the guidewire does not enter the assembly through the access port.

Figure 25:
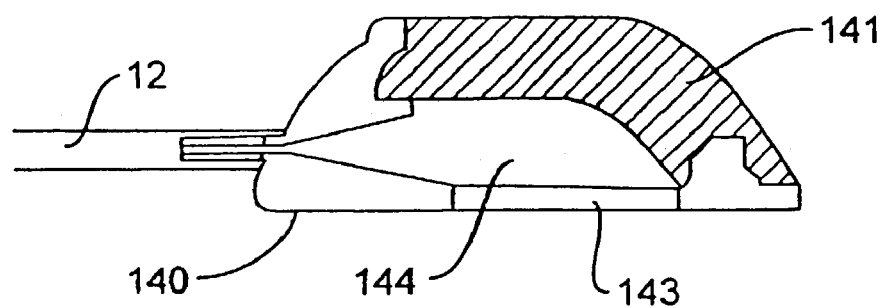
FIG. 25 is a side cross section view of an access port and catheter in accordance with a ninth embodiment of the present invention.
Figure 26:
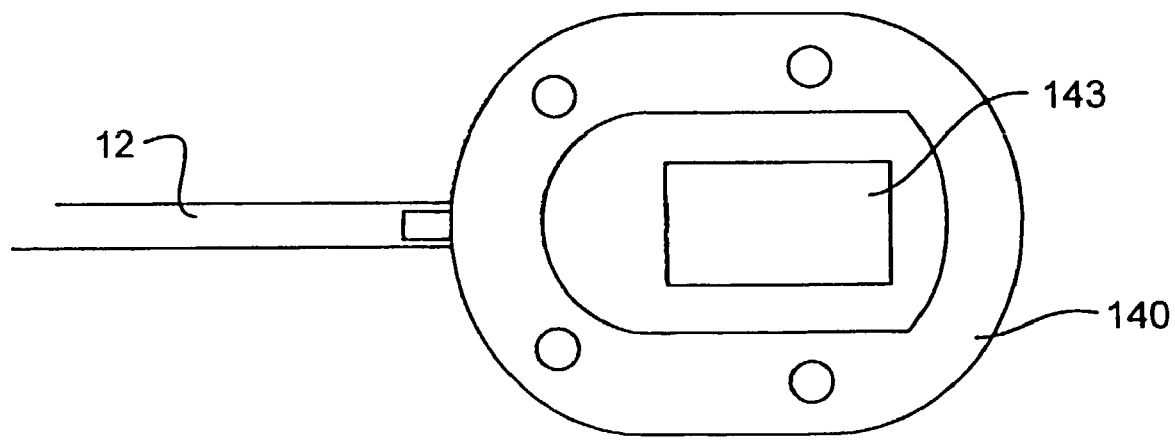
FIG. 26 is a bottom view of the access port of FIG. 25.
Figure 27:
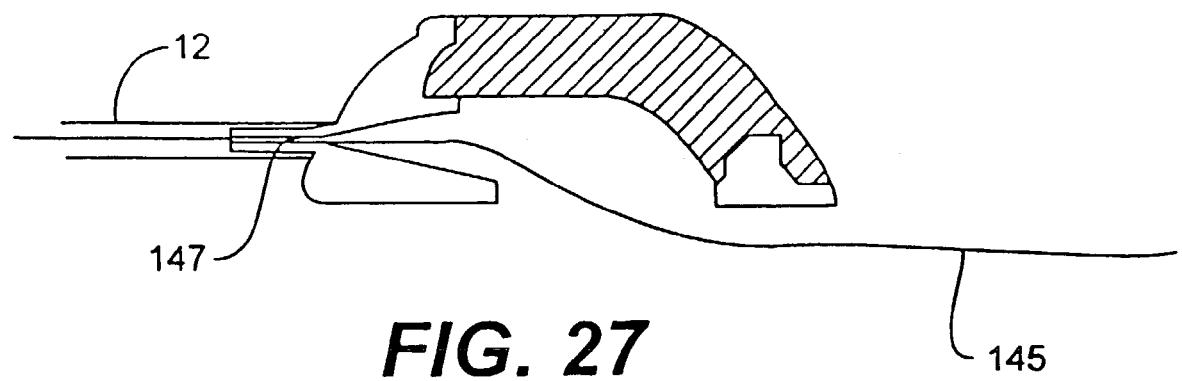
FIG. 27 is a side cross section view of the access port of FIG. 25 with the bottom plate removed and a guidewire or stylet inserted.
Figure 28:
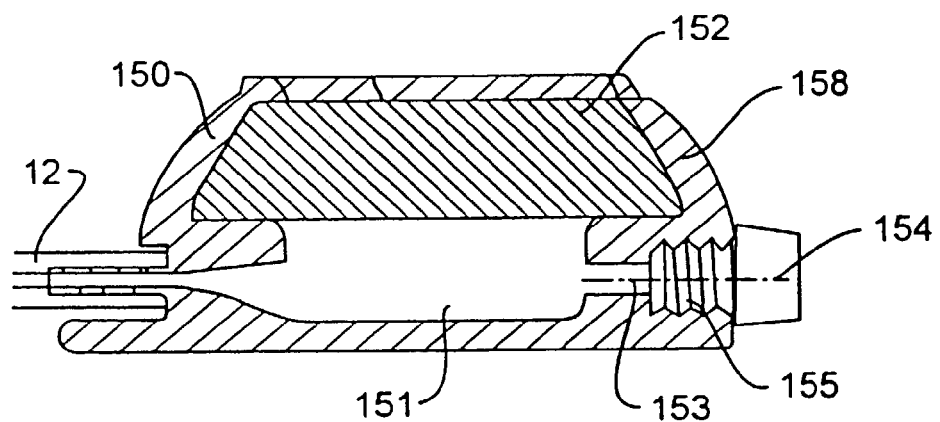
FIG. 28 is a side cross section view of an access port and catheter in accordance with a tenth embodiment of the present invention.
Figure 29:
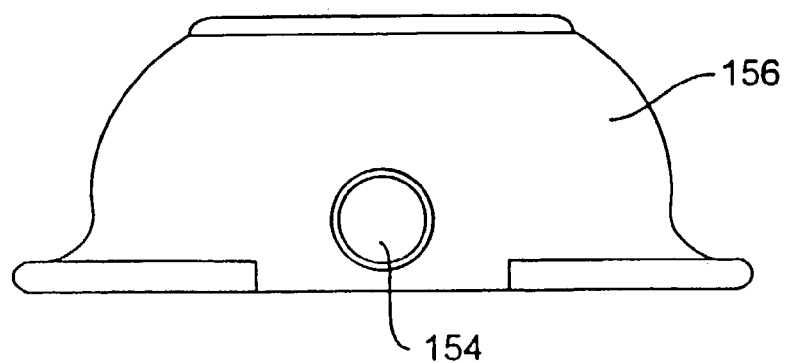
FIG. 29 is a rear view of the access port of FIG. 28.

FIGS. 25–27 illustrate an embodiment of the present invention in which access port 140 having soft bodied septum 141 is provided with a removable panel 143 to give open access to reservoir 144. As shown in FIG. 27, removal of panel 143 from the bottom of port 140 opens reservoir 144 to permit insertion of guidewire 145 through the reservoir and into opening 147 into the lumen of catheter 12.

Figure 30:
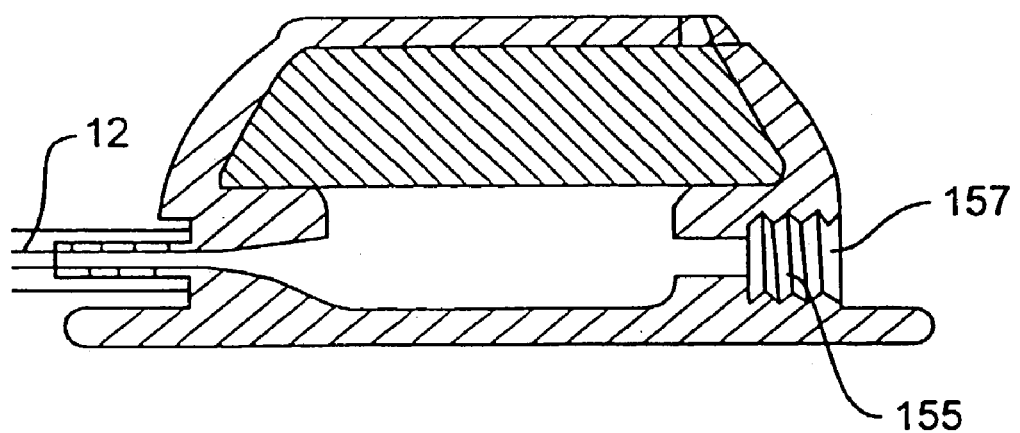
FIG. 30 is a side cross section view of an access port and catheter in accordance with an eleventh embodiment of the invention.
Figure 31:
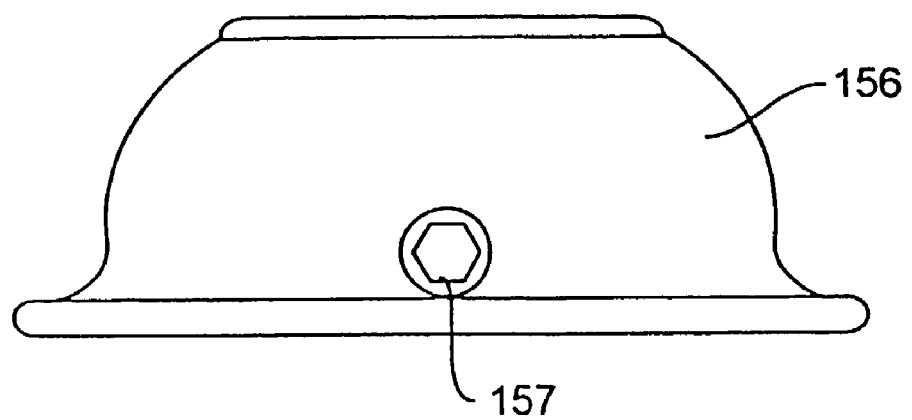
FIG. 31 is a rear view of the access port of FIG. 30.

FIGS. 28–31 illustrate a further embodiment of the present invention in which access to reservoir 151 in access port 150 having soft septum 152 disposed within hard body 158 is through channel 153 which is otherwise closed by threaded bolt 54 in hole 155 at the back side 156 of the access port. Removal of bolt 154 allows a guidewire or stylet (not shown) to be inserted in a direct line through reservoir 151 into catheter 12. FIGS. 30 and 31 illustrate the alternative use of a recessed set screw or plug 157 in hole 155.

Figure 15:
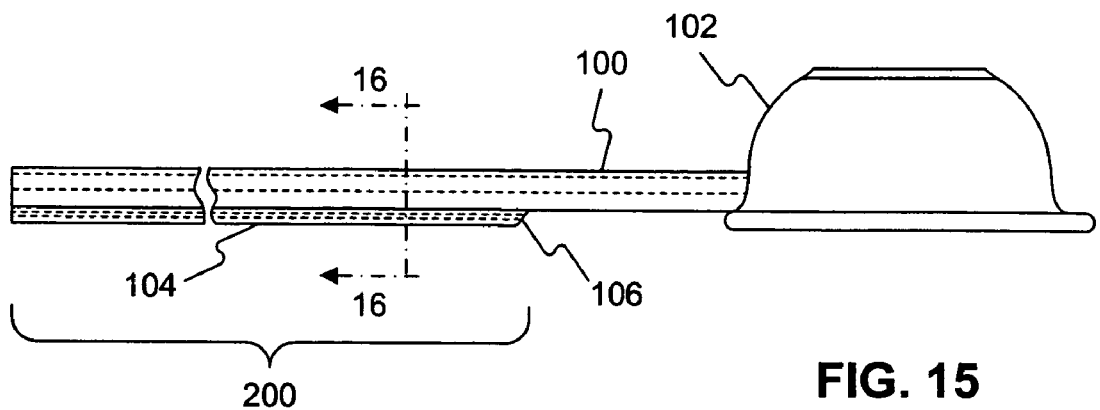
FIG. 15 is a side view of an access port and catheter in accordance with a fifth embodiment of the present invention.
Figure 16:
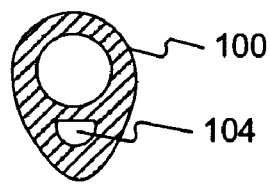
FIG. 16 is a cross sectional view of the catheter of FIG. 15.

As shown in FIGS. 15–16, the catheter 100, fixedly attached to the access port 102, has portion 200 including a truncated lumen 104 located on the underside of catheter 100. Truncated lumen 104 is shown on the underside of catheter 100 in FIGS. 15–16, but could be located anywhere around the periphery of catheter 100, i.e., the side, the top, etc. As with the previous embodiments, the catheter 100 is cut to length by using a measuring wire or guidewire to determine the correct length from the insertion point to the location point, e.g., superior vena cava. After the catheter 100 is cut to an appropriate length, a guidewire is inserted into and through the truncated open lumen 104 through opening 106. The guidewire (not shown) is then inserted into the patient at the insertion point and advanced to the desired location in the patient. The access port 102 and catheter 100 are then slid over and along the guidewire and inserted into the patient as described before. Similarly, the guidewire could first be inserted into the patient and the catheter then slipped over the inserted guidewire. Depending on the type of use and location of use, the length of lumen 104 may vary from very short to the entirety of the catheter. When the lumen 104 is shorter than the length of catheter 100, its position along the catheter may also vary depending on the type of trimming, method of insertion, etc.

Figure 17:
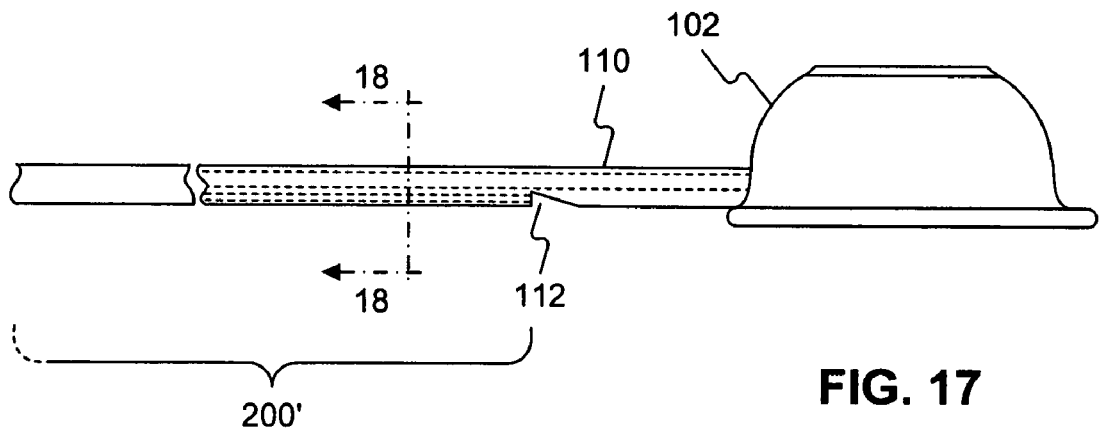
FIG. 17 is a side view of an access port and catheter in accordance with a sixth embodiment of the present invention.
Figure 18:
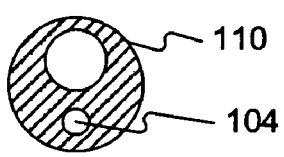
FIG. 18 is a cross sectional view of the catheter of FIG. 17.
Figure 19:
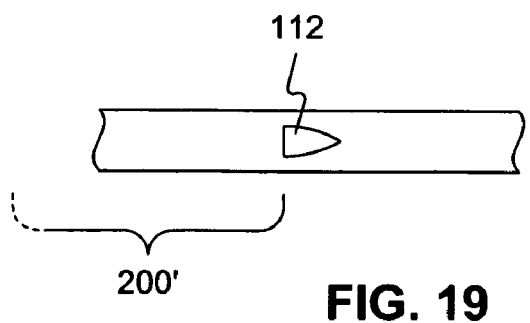
FIG. 19 is a bottom view of a portion of the catheter of FIG. 17.

FIGS. 17–19 show an alternative multi-lumen catheter 110 attached to an access port 102 (again, any access port would be acceptable). Rather than the truncated open lumen 104 as in the previous embodiment, multi-lumen catheter 110 has a skive 112 allowing access to a guidewire (not shown) into a secondary lumen 114. The catheter 110 includes a portion 200' extending in a distal direction from the skive 112 and including the secondary lumen 114. The combination of the access port 102 and catheter 110 are inserted and secured into the patient in substantially the same manners as described for the previous embodiments. The skive 112, or opening, could be located anywhere along the length of the catheter between the access port 102 and the distal end of the catheter. Additionally, the secondary lumen 114 could be located anywhere around the circumference of catheter 110.

Figure 21:
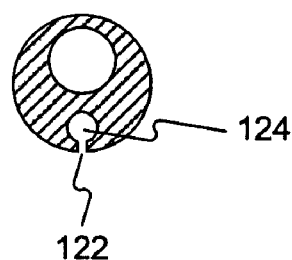
FIG. 21 is a cross sectional view of the catheter of FIG. 20.
Figure 21A:
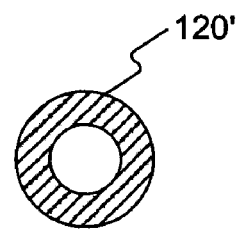
FIG. 21a is a schematic cross-sectional view similar to FIG. 21 showing a single lumen catheter.

An alternate but related way to insert an access port/catheter assembly is using a guidewire with a single lumen catheter, such as the catheter 120' shown schematically in FIG. 21a. Rather than having the second lumen, the guidewire could be inserted into the side wall of the single lumen catheter. Preferably, if the catheter is made from resealable materials so that the guidewire can be inserted anywhere along the length of the catheter (with or without a needle) and subsequently removed without leakage. Alternatively, the catheter could have a resealable, predetermined area, band, or section into which the guidewire could be inserted. After the guidewire is inserted into the catheter, the guidewire would be advanced to the desired location and the catheter advanced over the guidewire to that same location. If the insertion point is near the access port, the physician would be able to ensure that the catheter has resealed itself after the guidewire/needle is removed. On the other hand, if the access point for the guidewire were closer to the distal end of the catheter, then resealing properties of the catheter may not be as important since the hole would be close to the target area.

Figure 20:
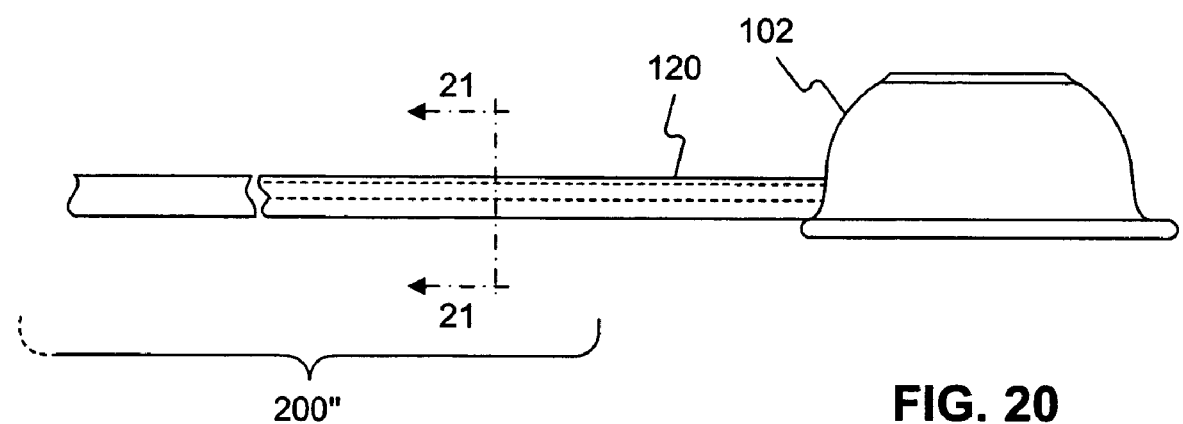
FIG. 20 is a side view of an access port and catheter in accordance with a seventh embodiment of the present invention.
Figure 22:
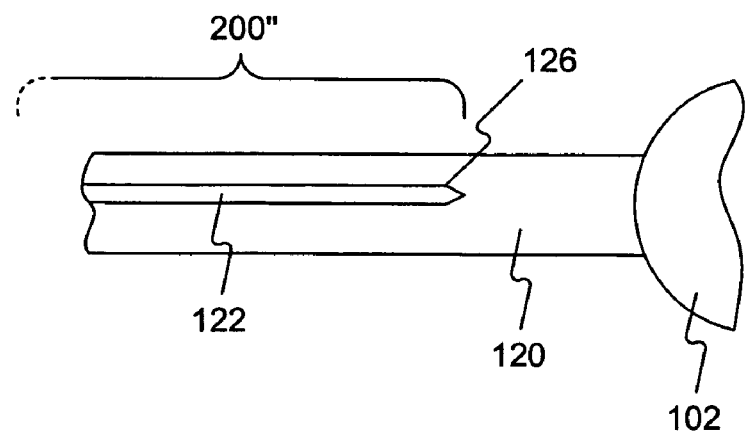
FIG. 22 is a bottom view of a portion of the catheter of FIG. 20.

Another embodiment of the present invention is shown in FIGS. 20–22 including an access port 102 and catheter 120. Rather than the truncated open lumen 104 or multi-lumen catheter 110 with a skive 112 as in the previous two embodiments in FIGS. 15 and 17 respectively, this embodiment has a portion 200" extending in a distal direction from an opening 126 (FIG. 22) and including a narrow slit 122 along the underside of catheter 120 leading into secondary lumen 124. The slit 122 could also be placed anywhere around the catheter 120. The side portions of slit 122 should be close together to prevent the guidewire from slipping out of the secondary lumen 124. In some instances the resilient sides of slit 122 may actually touch to close the slit. The physician could insert the guidewire (not shown) in one of several ways. First, after determining appropriate length for catheter 120, the physician could insert the guidewire at a distal end of catheter 120 and continue to feed the guidewire into the secondary lumen 124 until it exited catheter 120 at the opening 126. Alternatively, the physician could also press the guidewire into secondary lumen 124 through slit 122 along the entire length of the appropriately trimmed catheter 120. Once the catheter has been inserted and placed into the patient, the guidewire can be removed by sliding the guidewire out through slit 122 or opening 126. Depending upon the geometries encountered by the physician, the guidewire can come out of the secondary lumen 124 at any point along the slit 122 as required.

It will be apparent to those skilled in the art that various modifications and variations can be made in the apparatus and method of the present invention without departing from the spirit or scope of the invention. Thus, it is intended that the present invention cover the modifications and variations of this invention provided they come within the scope of the appended claims and their equivalents.

What is claimed is:

1. An access port assembly comprising:
    an access port comprising a self-sealing access septum and a reservoir; and
    a catheter having a proximal end and a distal end opposite to the proximal end, the proximal end of the catheter being fixedly attachable to the access port, the catheter comprising:
        a lumen in flow communication with the port when the proximal end of the catheter is attached to the access port,
        an entry site located between the proximal and distal ends of the catheter, and
        a portion extending in a distal direction from the entry site toward the distal end of the catheter,
        wherein the catheter is configured to accept and pass a guidewire directly from an exterior of the catheter to said portion via the entry site,
        wherein the catheter has an opening at a distal end of the portion, the catheter being configured so that a guidewire passing through the entry site is capable of exiting the catheter via the opening,
        wherein the lumen is a first lumen of the catheter, and wherein the portion comprises a second lumen of the catheter.

2. The access port assembly of claim 1, wherein the first lumen lacks flow communication with the second lumen.

3. The access port assembly of claim 1, wherein the first and second lumens extend through the portion.

4. The access port assembly of claim 1, wherein the first lumen extends in the distal direction from the proximal end of the catheter and through the portion.

5. The access port assembly of claim 1, wherein the entry site is configured to be resealable so that the entry site reseals when the guidewire is removed from the entry site.

6. The access port assembly of claim 1, wherein the self-sealing access septum is configured to permit a needle to be inserted through the septum by inserting the needle into the septum and moving the needle in a direction facing the reservoir, and wherein the septum is configured to reseal when the needle is removed from the septum by moving the needle in a direction facing away from the reservoir.

7. A method for inserting an access port assembly into a patient's body, comprising:
 providing a system comprising:
  a guidewire; and
  an access port assembly comprising:
   an access port comprising a self-sealing access septum and a reservoir; and
   a catheter having a proximal end and a distal end opposite to the proximal end, the proximal end of the catheter being fixedly attachable to the access port, the catheter comprising:
    a lumen in flow communication with the port when the proximal end of the catheter is attached to the access port,
    an entry site located between the proximal and distal ends of the catheter, and
    a portion extending in a distal direction from the entry site toward the distal end of the catheter,
    wherein the catheter is configured to pass said guidewire directly from an exterior of the catheter to said portion via the entry site;
 inserting the guidewire into the entry site such that the guidewire extends along said portion of the catheter and through the entry site;
 inserting the guidewire into the patient's body; and
 manipulating the access port assembly over the inserted guidewire.

8. An access port assembly comprising:
 an access port comprising a self-sealing access septum and a reservoir; and
 a catheter having a proximal end and a distal end opposite to the proximal end, the proximal end of the catheter being fixedly attachable to the access port, the catheter comprising
  a first lumen in flow communication with the port when the proximal end of the catheter is attached to the access port,
  an entry site located between the proximal and distal ends of the catheter, and
  a portion extending in a distal direction from the entry site toward the distal end of the catheter,
  wherein the catheter is configured to accept and pass a guidewire directly from an exterior of the catheter to said portion via the entry site,
  wherein the portion comprises a second lumen of the catheter, and
  wherein the second lumen is not in flow communication with the port when the proximal end of the catheter is attached to the access port.

9. The access port assembly of claim 8, wherein the catheter is configured to pass the guidewire into the second lumen via the entry site.

10. The access port assembly of claim 8, wherein the self-sealing access septum is configured to permit a needle to be inserted through the septum by inserting the needle into the septum and moving the needle in a direction facing the reservoir, and wherein the septum is configured to reseal when the needle is removed from the septum by moving the needle in a direction facing away from the reservoir.

* * * * *